United States Patent [19]
Morgan et al.

[11] Patent Number: 5,749,731
[45] Date of Patent: May 12, 1998

[54] APPARATUS FOR PRESERVING INTERDENTAL PAPILLA AND METHOD FOR USING

[75] Inventors: Vincent J. Morgan, Boston; Norman J. Shepherd, Merrimack, both of Mass.

[73] Assignee: DIRO, Inc., Boston, Mass.

[21] Appl. No.: 586,951

[22] Filed: Jan. 16, 1996

Related U.S. Application Data

[63] Continuation-in-part of Ser. No. 293,308, Aug. 22, 1994, Pat. No. 5,499,918.

[51] Int. Cl.⁶ .................................................. A61C 8/00
[52] U.S. Cl. ................................... 433/173; 433/172
[58] Field of Search ............................. 433/173, 174, 433/175, 176, 172

[56] References Cited

U.S. PATENT DOCUMENTS

| | | | |
|---|---|---|---|
| 4,293,302 | 10/1981 | Hassler et al. | 433/173 |
| 4,531,916 | 7/1985 | Scantlebury et al. | 433/176 |
| 4,738,623 | 4/1988 | Driskell | 433/173 |
| 5,104,318 | 4/1992 | Piche et al. | 433/173 |
| 5,286,195 | 2/1994 | Clostermann | 433/172 |
| 5,297,963 | 3/1994 | Daftary | 433/172 |
| 5,344,457 | 9/1994 | Pilliar et al. | 433/174 |

*Primary Examiner*—Cary E. O'Connor
*Attorney, Agent, or Firm*—John A. Haug

[57] ABSTRACT

An emergence cuff (30,30') formed of suitable biocompatible synthetic plastic is shown having a bore adapted to be received on an abutment in turn mounted on a root marker implanted in the alveolar ridge of a patient. The cuff has a bore (36) generally matching the crown receiving surface of the abutment and an outer surface which goes from a feathered edge portion with the bore a first end (34,34') closest to the root member and a larger outer surface at the second end. The gum tissue is sutured onto the cuff and abutment so that after sufficient healing when the cuff is removed a sulcus is formed to receive a crown with the interface of the crown and the abutment located below the gum line. The emergence cuff can also serve as the cervical portion of a temporary crown (40) by attaching it thereto as by using a mechanical interlock (39), if desired. An optional radially inwardly extending flexible lip (48) is shown at the first end to provide a positive seat for the cuff member on the abutment.

5 Claims, 2 Drawing Sheets

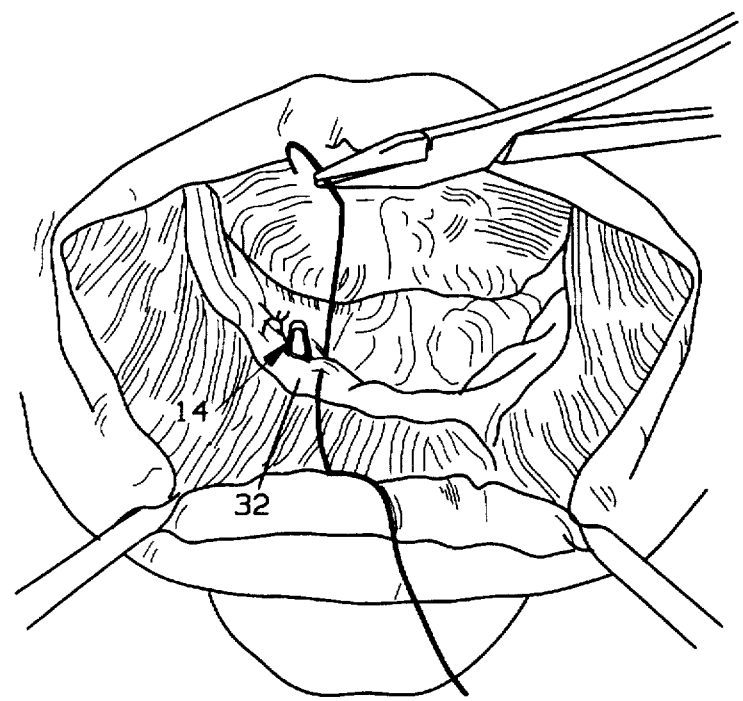
FIG 3
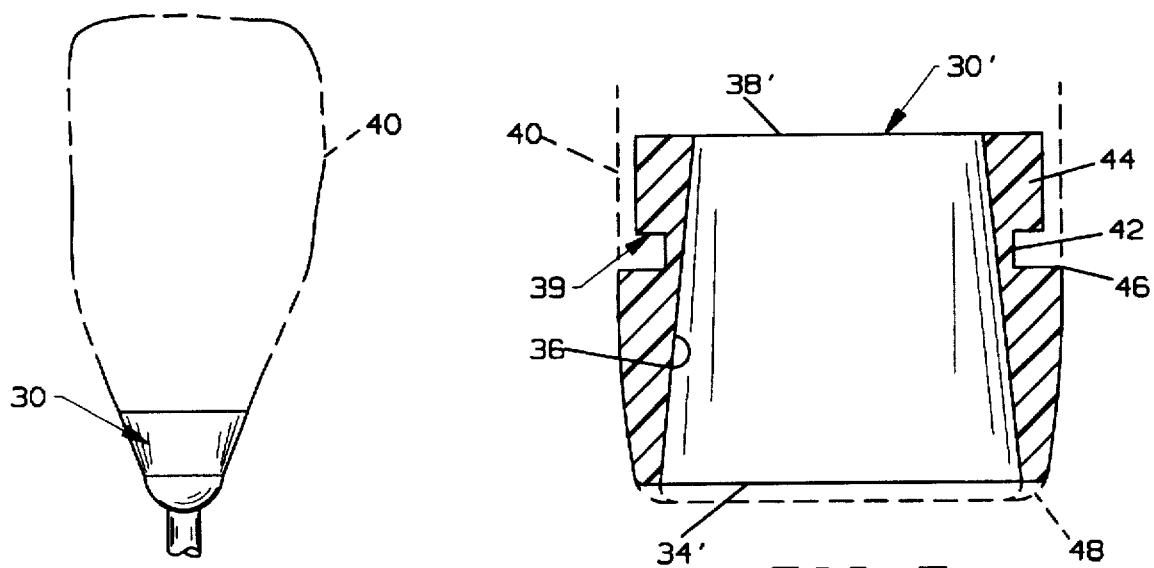
FIG 4
FIG 5

APPARATUS FOR PRESERVING INTERDENTAL PAPILLA AND METHOD FOR USING

BACKGROUND

This is a continuation-in-part of U.S. application, Ser. No. 08/293,308, filed Aug. 22, 1994, now U.S. Pat. No. 5,499,918.

This invention relates generally to restorative dentistry and more particularly to implant prosthetic procedures.

The natural teeth of an individual are often lost as a result of dental disease or trauma, making it desirable to replace a natural tooth with a prosthetic device. One type of prosthetic device is a dental implant which is surgically positioned within the mandibular or maxillary alveolar bone of the patient and, after healing, is fitted with a tooth-simulating prosthesis or crown.

One type of dental implant, often called a submergible or two stage implant, has a separate root member which is implanted by an oral surgeon in the alveolar bone of the patient. Following healing, a head member or abutment is mounted on the root and then the crown is mounted on the abutment.

An implant of this type which has become widely used is shown and described in co-assigned U.S. Pat. No. 4,738,623. In this patent a root member having multiple, outwardly extending fins formed on the lower portion thereof has a narrowed upwardly and inwardly contoured shoulder formed above the fins and an abutment receiving female seat or socket formed through the top of the shoulder. Upon surgical insertion, autogenous graft material including conventional synthetic grafting material is packed in the void surrounding this narrowed shoulder. A small healing plug is positioned in the socket while the gingiva is permitted to heal over the entire implant.

When sufficient healing has occurred, i.e., in several months, the plug is surgically accessed and removed. A permanent abutment member having a male or post portion such as those formed with a locking taper, is then mounted on the root member with the post portion received in the socket, in the cited example, a socket formed with a locking taper. The abutment or head member has an upstanding generally tapered, conical exterior surface with an anti-rotational flat surface portion for mounting the prosthetic crown and a basal portion having a convex, frusto-spherical exterior surface which extends downwardly from the tapered portion. The center of the sphere which defines the frusto-spherical surface lies on the axis of the conical surface so that the frusto-spherical and conical surfaces intersect along a circle. When surgically implanted the spherical surface extends through the gingiva and alveolar crest toward the root member and provides an interface between the tissue and the abutment which has a circular cross section, regardless of alignment of the head member.

The healing plug is surgically accessed by excising the tissue over the plug, for example by using a small round bur or a scalpel and is removed by retracting the plug with forceps or using a conventional 700XL bur pressed into the center of the plug and turning the bur clockwise slightly. The site is then prepared as by using a sulcus reamer corresponding to the diameter of the basal portion to remove excess bone overlying the implant so that the head may be fully seated. After appropriate flushing and drying of the root socket the post portion of the head is inserted. If a flap procedure was used to access the submerged implant the flaps are trimmed to accommodate the protruding implant head and then stitched together with interrupted sutures and allowed to heal. The gum tissue is allowed to heal while the permanent crown is prepared using conventional techniques including the taking of an impression.

However, a problem frequently occurs regarding the interdental papilla. That is, the gum tissue tends to heal taut to the head of the abutment member so that when the permanent crown is placed on the abutment member the margin of the crown is not concealed. This negative aesthetic effect is exacerbated by the fact that conventional implants have a given width smaller than the teeth they replace. For example, in the anterior part of the mouth a central incisor is typically on the order of 8 mm across at the gum line and typical implants for such teeth are on the order of 4 mm at the location extending from the gum tissue. As a result an undesirable triangular apex configuration typically forms at the gum line detracting from the cosmetic appearance.

SUMMARY OF THE INVENTION

It is an object of the present invention to provide an implant procedure which will preserve the interdental papilla or gum profile associated with natural teeth and apparatus for use with such procedure.

It is known to use so called healing abutments which comprise various pieces of metal to provide a selected shape which are placed on the root member while the gum is allowed to heal and are then replaced with a permanent abutment having a smaller configuration to leave a sulcus adapted to receive a crown with the margin disposed subgingivally. However, this system requires a prolonged period for healing due to the metal structure and is not conducive for use with a temporary crown. A suitable, cosmetically pleasing temporary crown is desirable so that the patient can effectively participate in public during the interim time between initially inserting the abutment and the time when the permanent crown is installed.

It is therefore another object of the invention to provide an implant procedure and apparatus for preserving the interdental papilla associated with natural teeth which does not have the prior art limitations noted above.

Briefly, according to the invention, an annular cuff formed of suitable biocompatible material, such as methylmethacrylate or nylon is placed on a permanent abutment member at the time the abutment is mounted on the root member and the gum tissue is then sutured over the cuff and abutment member and allowed to heal. The cuff has a tapered bore essentially matching that of the crown mounting conical portion of the abutment member, i.e., a taper generally approximately 7 degrees, and an outer surface going from a feathered edge at a first circular end adapted to serve as a smooth continuation of the frusto-spherical surface of the basal portion of the abutment member to a second circular end at a selected height of approximately 3 mm having a selected larger diameter, preferably approximately 3 mm larger than the first end. In cross-section this surface may form a straight line as seen in FIG. 2 or a curved line as seen in FIG. 5. After sufficient healing, e.g., two or three weeks, the gingiva is formed tautly about the cuff. The cuff can thereafter be removed leaving a sulcus having a predetermined, optimized shape. The dentist can then take an impression and cement the crown a couple of millimeters below the gum line for a cosmetically pleasing result. The precise fit of the cuff insures that iritation of the gum tissue is minimized. Use of the cuff also enables the dentist to cement or otherwise bond a temporary crown to the cuff at the time of placement on the abutment. The cuff may be formed with a retaining groove at its second end to form a mechanical locking bond, for example.

Additional objects and features of the invention will be set forth in part in the description which follows and in part will be obvious from the description. The objects and advantages of the invention may be realized and attained by means of the instrumentalities, combinations and methods particularly pointed out in the appended claims.

BRIEF DESCRIPTION OF THE DRAWINGS

The accompanying drawings, which are incorporated in and constitute a part of the specification, illustrate preferred embodiments of the invention and, together with the description, serve to explain the objects, advantages and principles of the invention. In the drawings:

FIG. 3 is a perspective view of a patient's mouth in which the gingiva is being sutured about a cuffed abutment;

FIG. 4 is an enlarged elevational view of a cuff attached to a temporary crown (shown in phantom); and FIG. 5 is a cross-sectional view of a cuff made in accordance with a modified embodiment.

DETAILED DESCRIPTION OF PREFERRED EMBODIMENTS

Figure 1:
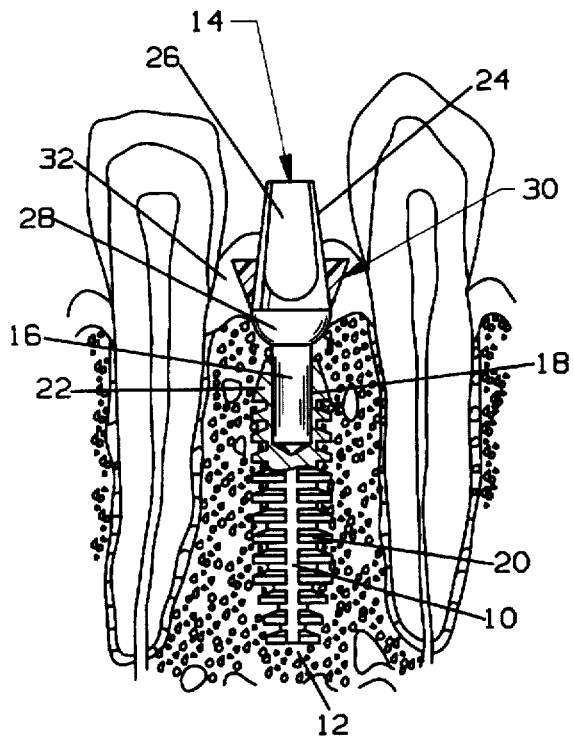
FIG. 1 is an enlarged elevational view, partly in cross-section, of a root member implanted in the alveolar ridge with an abutment member mounted thereon and having a gum profile preserving cuff disposed on the abutment member made in accordance with the invention.

With reference to FIG. 1 a root member 10 is shown implanted in the alveolar bone 12 of a patient in the manner taught in U.S. Pat. No. 4,738,623, referenced above. Head or abutment member 14 is mounted on the root member by means of a post 16 having a locking taper received in socket or bore 18 of root member 10, the bore having a matching locking taper. The root member has a plurality of outwardly extending fins 20 formed on the lower portion thereof and a narrowed upwardly and inwardly contoured shoulder 22 formed above the fins.

Abutment member 14 has an upstanding, generally tapered, conical exterior surface 24 with an anti-rotational flat surface 26 for mounting a prosthetic crown and a basal portion 28 having a convex, frusto-spherical exterior surface which extends downwardly from the tapered portion. The center of the sphere which defines the frusto-spherical surface lies on the axis of the conical surface so that the fruso-spherical and conical surfaces intersect along a circle. The frusto-spherical surface is disposed on a seat formed in the alveolar crest with post 16 extending into socket 18 and locked therein.

Figure 2:
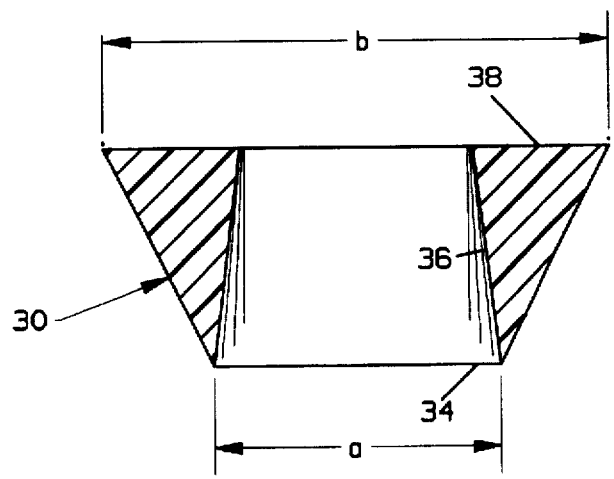
FIG. 2 is a greatly enlarged cross-sectional view of the FIG. 1 cuff.

Interdental profile preserving cuff 30, see also FIG. 2, formed of suitable biocompatible material, such as methylmethacrylate or nylon is disposed on abutment member 14 with gingiva 32 sutured onto the cuff and abutment member as shown in FIG. 3. After a short time, normally one to two weeks, the gingiva heals taut around the abutment member and cuff. The site is accessed and cuff 14 removed leaving a sulcus having a predertermined configuration matching that of the crown to be installed and so that the interface of the crown will be located below the gum line. The dentist then takes an impression in the conventional manner for preparation of a permanent crown and a suitable temporary crown, having the same interfacial surface determined by the cuff, is placed on head portion 24 resulting in minimal irritation of the gum tissue.

Abutments of the type disclosed in the above referenced patent are provided in several standard sizes, for example, the diameter of the frusto-spherical portion of three such sizes are 4, 5, and 7.5 mm respectively. The conical surface portion 24 has a taper of approximately 7 degrees. The cuff is configured so that it fits on the conical surface 24 with a first end 34 closest to the basal portion 28 received at or slightly spaced from the intersection of the frusto-spherical and conical portions on the conical surface side of the intersection. The cuff has an internal bore 36 effectively matching the taper of the conical surface 24, i.e., it has a taper of approximately 7 degrees and a height of appproximately 3 mm. The outer diameter of second end 38 is approximately 3 mm greater than that of end 34 which comes to a feathered edge with bore 36. The outer surface of the cuff between the two ends is formed with a smooth surface, generally frusto-conical, however, it will be appreciated that the surface could also be formed as a convex curved surface as shown in FIG. 5 to be discussed below. This results in a sulcus which matches that of a permanent crown to be received on abutment 14 so that the interface of the crown with the abutment is well below the final profile of the gum tissue, e.g., 1–2 mm below.

Suitable dimensions for cuffs used with the above referenced abutments are shown in table 1 below.

TABLE 1

| a | b | height | taper of bore 36 |
|---|---|---|---|
| 4 mm | 7 mm | 3 mm | 7 degrees |
| 5 mm | 8 mm | 3 mm | 7 degrees |
| 7.5 mm | 10.5 mm | 3 mm | 7 degrees |

It will be appreciated that cuff 30 could be used with various other types of abutments with suitable changes being made in the above dimensions. For example, the cuffs could be used with abutments of the type which are threadingly received on a root member. Cuffs made in accordance with the invention can be easily adjusted by the dentist at chairside, as by adding to or reducing from a cuff, to accommodate specific situations.

Cuff 30 may also serve as the cervical portion of a temporary crown 40 by cementing, cross-linking or otherwise bonding the cuff to a coronal portion, as depicted in FIG. 4, and placed on the abutment therewith. For example, with reference to FIG. 5, a cuff 30' is shown having locking means 39 for attaching temporary crown 40. Locking means 39 comprises a generally annular groove 42 adjacent second end 38' forming a radially extending retaining flange 44 which has an outer diameter which is reduced somewhat relative to the other side 46 of groove 42 in order to allow crown 40 to be formed over flange 44 with the outer surface of crown 40 forming a continuous smooth surface with cuff 30'.

Temporary crown 40 may be formed by placing a mold containing a mixture of suitable powder and liquid, e.g., methylmethacralate, against the cuff and allowed to set in situ. Excess polymer which overflows may trimmed away before and/or after setting.

Cuff 30' may also be formed with an inwardly extending, circumferential, flexible lip 48, shown in dashed lines in FIG. 5. Lip 48 slides onto the undercut of the abutment, i.e., beyond the greatest circumferential portion, to provide a positive seat for the cuff thereby minimizing any tendencies of the soft tissue of the patient to displace the cuff during the suturing procedure.

Use of the cuff not only results in an improved interdental papilla it also makes the impression procedure and fitting of the permanent crown much less critical and less likely to cause undesirable gum irritation and possible periodontal problems. The dentist can take the impression, have a permanent crown fabricated and cement the crown in place knowing that the shape of the contour of the interface will be below the gum line because it is predetermined by the cuff.

Although the invention has been described with regard to specific preferred embodiments thereof, variations and modifications will become apparent to those skilled in the art. It is therefore the intention that the appended claims be interpreted as broadly as possible in view of the prior art to include all such variations and modifications.

What is claimed:

1. An emergence cuff member for use in preserving the interdental papilla during the procedure of placing an abutment on a root member implanted in the alveolar bone of a patient in which the abutment has a frusto-spherical basal surface portion and a conical surface portion having a selected height extending therefrom comprising a generally annular member formed of biocompatible synthetic plastic having first and second ends, a bore extending from the first to the second ends, the bore having a taper generally matching that of the conical surface portion of the abutment, the larger end of the bore being at the first end, the outer surface of the annular member forming a feathered edge with the bore at the first end of the annular member, the distance between the first and second ends being less than the height of the conical surface, the diameter of the cuff member increasing in the direction going from the first end to the second end, and locking means formed at the second end to lock a temporary crown thereto.

2. An emergence cuff member according to claim 1 in which the locking means comprises a radially extending retaining member.

3. An emergence cuff member according to claim 1 in which the locking means comprises a generally annular groove formed around the periphery of the cuff member in which the member on the side of the groove closest to the second end has a reduced diameter.

4. An emergence cuff member according to claim 1 further including a radially inwardly extending flexible lip formed at the first end of the cuff member.

5. An emergence cuff member for use in preserving the interdental papilla during the procedure of placing an abutment on a root member implanted in the alveolar bone of a patient in which the abutment has a frusto-spherical basal surface portion and a conical surface portion having a selected height extending therefrom comprising a generally annular member formed of biocompatible synthetic plastic having first and second ends, a bore extending from the first to the second ends, the bore having a taper generally matching that of the conical surface portion of the abutment, the larger end of the bore being at the first end, the outer surface of the annular member forming a feathered edge with the bore at the first end of the annular member, the distance between the first and second ends being less than the height of the conical surface, the diameter of the cuff member increasing in the direction going from the first end to the second end, and a radially inwardly extending flexible lip formed at the first end of the cuff member.

* * * * *